United States Patent [19]
Kawasaki et al.

[11] Patent Number: 5,674,993
[45] Date of Patent: Oct. 7, 1997

[54] NUCLEIC ACID MARKERS FOR RICE BLAST RESISTANCE GENES AND RICE BLAST RESISTANCE GENES ISOLATED BY THE USE OF THESE MARKERS

[75] Inventors: Shinji Kawasaki; Masaya Satoh; Naoki Katsura; Masaru Miyamoto; Ikuo Andoh, all of Ibaraki, Japan

[73] Assignees: National Institute Agrobiological Resources, Ministry of Agriculture Forestry and Fisheries, Ibaraki; Research Development Corporation of Japan, Saitama, both of Japan

[21] Appl. No.: 282,556

[22] Filed: Jul. 29, 1994

[30] Foreign Application Priority Data

Jul. 29, 1993 [JP] Japan ..................... 5-188544

[51] Int. Cl.⁶ .............. C12N 15/00; C12N 15/05; C12N 15/10
[52] U.S. Cl. .............. 536/23.6; 536/24.3; 536/24.33; 435/172.3; 935/2; 935/22; 935/27; 800/205
[58] Field of Search .............. 435/172.1, 172.3; 536/23.6, 24.33, 24.3; 935/2, 27, 22; 800/205

[56] References Cited

PUBLICATIONS

Hittalmani et al. "development of a PCR based marker to identify rice blast resistance gene, Pi-2(t), in a segregating population" Theor. Appl. Genet 91:9–14 1995.
Inukai et al. "Allelism of Blast resistace genes in near Isogenic lines of rice" Phytopathology pp. 1278–1283 1994.
Wang et al. RFLP "Mapping of Genes conferring complete and partial resistance to blast in a durably resistant rice cultivar" Genetics 13^: 1421–1434 Ap. 1994.

*Primary Examiner*—Gary Benzion
*Attorney, Agent, or Firm*—Wenderoth, Lind & Ponack

[57] ABSTRACT

The present invention provides nucleic acid markers for rice blast resistance genes, which are isolated from the rice genomic DNA, are DNA sequences having a total length of up to 2 kb, with two identical sequences of at least ten bases at the both ends thereof and are located within a distance of 2.0 cM from rice blast resistance genes Pi-b, Pi-ta or Pi-ta². According to the present invention, it becomes possible to easily isolate rice blast resistance genes and related genes from rice cultivars containing Pi-b, Pi-ta² or Pi-ta, thus promoting development and breeding of superior cultivars. It becomes also possible to easily carry out a resistance test of rice. This will open up the way to create new resistance genes.

6 Claims, 7 Drawing Sheets

NUCLEIC ACID MARKERS FOR RICE BLAST RESISTANCE GENES AND RICE BLAST RESISTANCE GENES ISOLATED BY THE USE OF THESE MARKERS

BACKGROUND OF THE INVENTION

1. Field of the Invention

The present invention relates to nucleic acid markers of rice blast resistance genes, and rice blast resistance genes isolated by use of these nucleic acid markers.

The rice blast resistance genes which can be marked by the nucleic acid markers of the present invention are very useful not only for the development of superior cultivar of rice, but also as a material for research and a genetic resource for creating new resistant genes capable of being introduced into various plants.

2. Description of Related Art

It is well known that there are genes rendering resistance against pathogens to plants, and introduction of these genes has been an important target in the conventional breeding efforts. As a result, many new types of cultivars have been created to date through introduction of these resistance genes. Importance of these resistance genes will further increase throughout the world as such biotic method to prevent epidemics by utilizing innate functions of plants will lower consumption of chemical pesticides, and is in accordance with promotion of human health and preservation of sound environments and still lowers the cost of agriculture.

Among the plant resistance genes against pathogens, the rice blast resistance gene was first discovered in Japan, and the presence of many such genes has been known thereafter. In particular, resistance genes derived from indica rice exhibit resistance to wide races of the rice blast fungi found in Japan, and are highly useful as genetic resources. Among others, Pi-b, Pi-ta and Pi-ta$^2$ genes derived from indica rice are suited for RFLP mapping of the genes. There are however still only a very limited cases of introduction into present elite cultivars.

The probable reasons are that the conventional breeding method requires many generations of backcrosses to introduce a resistance gene into a cultivar, accompanied with resistance tests by inoculating pathogens to many individuals every year. Application of a resistance test to pathogens of foreign-origin is almost impossible within Japan because of the strict control over import of foreign pathogens.

On the other hand, recent progress in plant biotechnologies has enabled to identify and isolate various genes, and then introduce them into other plants. For plant resistance genes also, therefore, if it was cloned it is not difficult to introduce them into any desired cultivars by genetic engineering techniques, and it will drastically reduce the time and labor required for breeding resistant cultivars. It will also be possible to clarify the mechanism how the resistance genes are working in plants, and making possible to modify the present gene and then provide new types of resistance genes. Many research groups are now making efforts to isolate resistant genes, but only a few have been successful to date. This is attributable to the fact that there is only limited information about the biochemical character of the resistance gene-products.

As a method for isolating genes, a technique known as positional cloning is now attracting the attention. This technique uses nucleic acid markers near a target gene in a genome map, and isolates target genes from a genome library. Actually, some of genes causing human hereditary human diseases have been isolated by the application of this technique.

Although only a few cases of success of this positional cloning have been reported in plants, rice is considered to be the most suitable plant for this technique for the following reasons: (1) rice has the smallest genome size among the major crops; (2) physical distance (in kb) corresponding to a unit genetic distance (cM) is very small in rice; (3) it is easy to limit the range of the gene location by utilizing several near isogenic lines (NIL) which have been developed by introgressing the indica derived genes into japonica background; and (4) it is easy to introduce genes into cells for complementation test.

An important key to successful of this positional cloning is whether or not a good adjacent markers are available. Calculating from the rice genome size and the genetic map, the physical distance corresponding to 1 centiMorgan (cM) of rice genetic map is estimated to be about 100–200 kb on nucleic acid basis. On the other hand, the average size of the insert of yeast artificial chromosome (YAC) is more than 200 kb. Therefore, if there is a DNA marker of the resistance genes within a distance of 100 kb, i.e., 0.5–1.0 cM, the possibility of success of positional cloning of the gene is considered to be very high.

Such nearby nucleic acid markers of rice blast resistance genes will be also useful for largely reducing the time and labor required for testing resistance in conventional breeding through backcrosses, for example.

SUMMARY OF THE INVENTION

The present invention has an object to provide novel nearby nucleic acid markers for rice blast resistance genes, and rice blast resistance genes isolated and cloned by the use of these markers.

The present invention provides nuclei acid markers for rice blast resistance genes, which are: isolated from rice genomic DNA; DNA sequences having a total length of up to 2 kb, with two identical sequences of at least ten bases at the both ends thereof; and located within a distance of 2.0 centiMorgan (cM) from rice blast resistance gene Pi-b, Pi-ta or Pi-ta$^2$.

The present invention also provides secondary nucleic acid markers located near the above-mentioned nucleic acid markers, and rice blast resistance genes and genes group associated with them isolated by the use of those markers.

According to the present invention, good markers for rice blast resistance genes Pi-b, Pi-ta$^2$ or Pi-ta are provided. By the use of these nucleic acid markers, it becomes possible to easily isolate rice blast resistance genes and related gene groups from various cultivars of rice, thus promoting development and breeding of superior cultivars. It is also possible to easily carry out a resistance test of rice. This will open up the way to create new resistant genes.

DETAILED DESCRIPTION OF THE INVENTION

Figure 1:
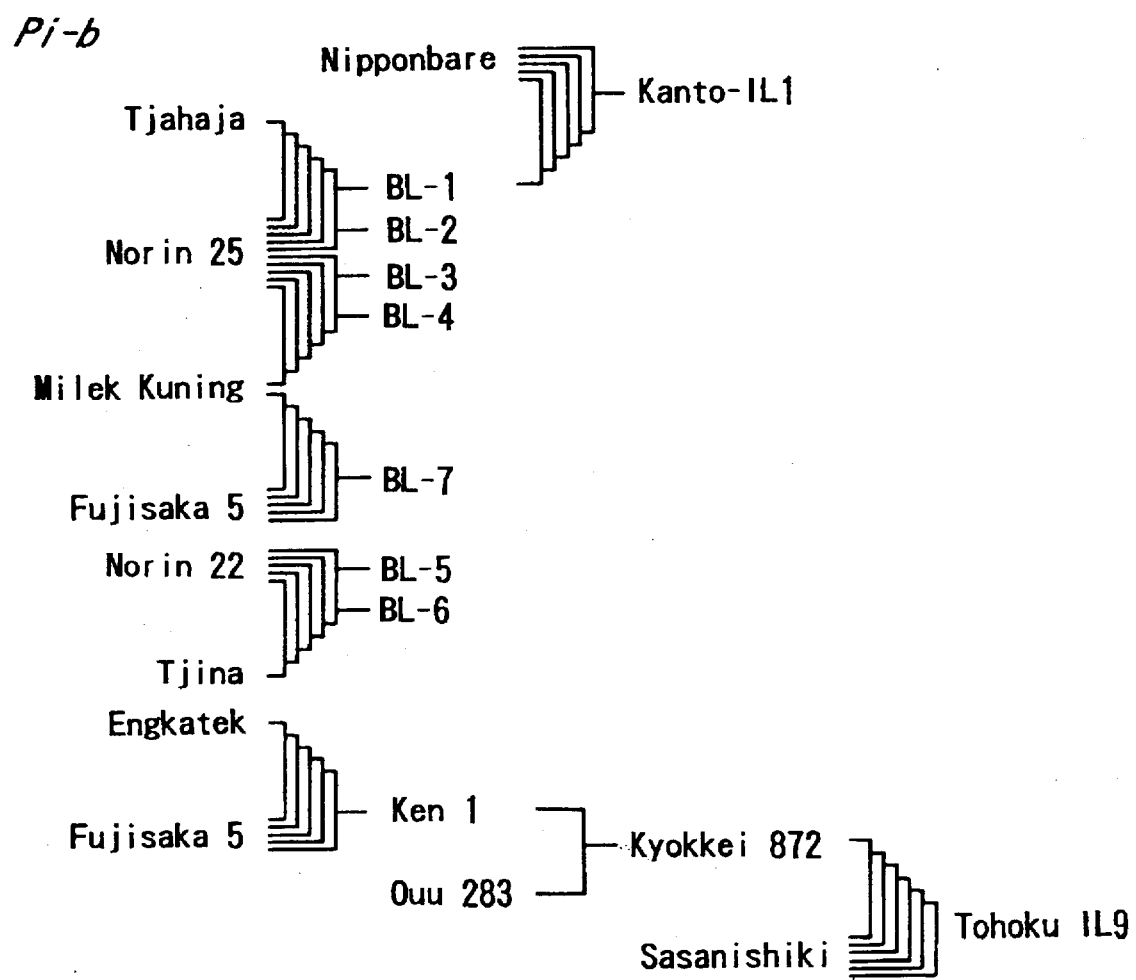
FIG. 1 is a pedigree illustrating the introduction of rice blast resistance gene Pi-b into japonica cultivars. Underlining indicates cultivars with the resistance gene.

The nucleic acid markers of the present invention are described further in detail below.

The nucleic acid markers of the present invention are obtained by comparing genomic DNAs of several different cultivars of rice with blast resistance gene Pi-b, Pi-ta or Pi-ta$^2$ and those of rice cultivars without the blast resistance genes, and identifying a specific DNA band present specifically in cultivars with rice blast resistance genes in the neighborhood (within 2.0 cM or about 200–400 kb) of rice blast resistance genes.

Comparison of genomic DNAs can be conducted between indica rice cultivars (donor parents) having rice blast resistance genes, and japonica rice cultivars (recurrent parents) not having such genes, and between rice cultivars of near isogenic lines developed by recurrent crossing the donor parent and the recurrent parent.

Furthermore, the nucleic acid markers of the present invention have characteristics that they are DNA sequences having total length of up to 2 kb, with identical sequences of at least ten bases at the both ends of them. More specifically, such nucleic acid markers can be identified after PCR-amplification of the genomic DNAs of the rice cultivars to be compared (for example, the above-mentioned donor parents, recurrent parents and near isogenic lines), using synthetic oligonucleotide primer of at least ten bases as primers, as the DNA fragments showing polymorphism linked to the target genes, especially those known to be in the neighborhood of the target genes with $F_2$ analysis.

The nucleic acid markers of the present invention thus prepared are DNA sequences having total length of up to 2.0 kb, with sequences same as to those of primers of PCR-amplification at the both ends of them, and are located within short distance of 2 cM from the rice blast resistance genes Pi-b, Pi-ta or Pi-ta$^2$, and serve as good labeling markers for rice blast resistance genes or related genes.

The present invention will be described below further in detail by means of Examples and Tests.

EXAMPLES AND TESTS

Example 1

A nucleic acid marker of rice blast resistance gene Pi-b was identified.

(1) Preparation of materials
(a) DNA extract:

The following extracts were prepared by known methods, respectively:

1) *Escherichia coli* plasmid DNA containing a rice library;
2) DNA of rice cultivars (donor parents) with the rice blast resistance gene Pi-b;
3) DNA of a japonica rice cultivars (recurrent parents) without the rice blast resistance gene Pi-b;
4) DNA of rice cultivars (near isogenic lines) developed by repeating crossing of the recurrent parents to the donor parents; and
5) Crude extract of leaves of the rice cultivars listed in 2),3) and 4) above.

(b) PCR primers:

An oligonucleotide primer with the sequence No. 1 nucleotide sequences was synthesized and employed.

(c) Solution of enzymate substrates for DNA amplification:

The composition and final concentrations are as follows:

Tris-Cl (pH: 8.3): 10 mM
KCl: 50 mM
MgCl$_2$: 2 mM
Gelatine: 0.01% (w/v)
dAPT, dTTP, dGTP, dCTP: 100 µM each
Taq polymerase: 0.5 units.

(2) Random PCR amplification of rice DNAs

Figure 6:
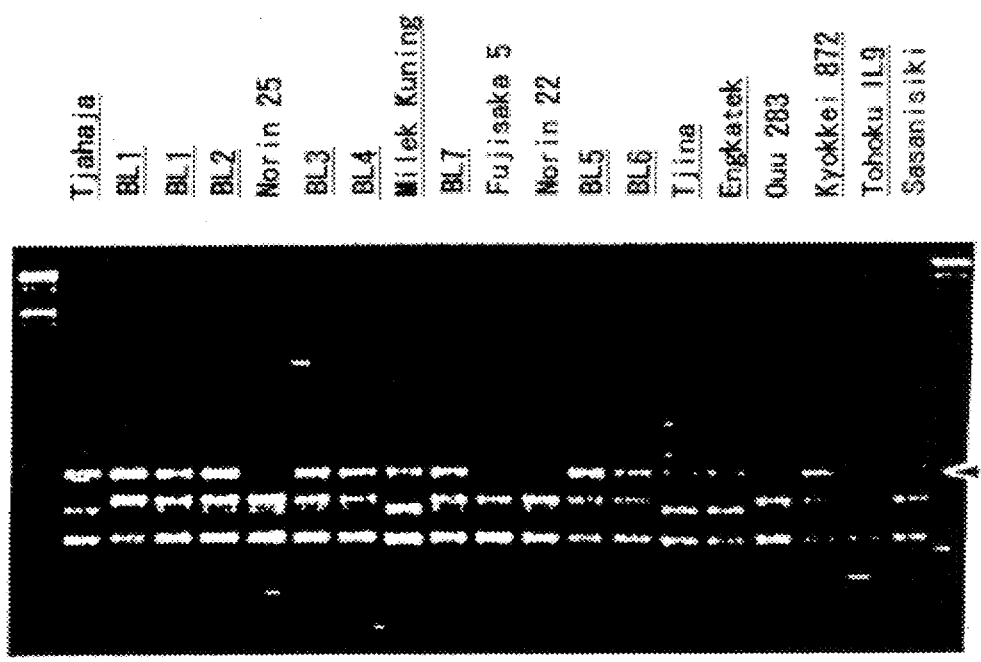
FIG. 6 is rapid marker b-1 band (arrow) amplified from the FIG. 1 related cultivars. Band b-1 is specific to the all of the cultivars with Pi-b as indicated by underlining.

Each of the DNA extracts 25 ng listed in (a)-1) to 5) above was mixed with 15 ng of primer (b) and 10 µl of 2.5 fold concentration of (c), and distilled water was added to make the total of 25 µl. The mixture in a reaction tube was subjected to 45 cycles of PCR cycle comprising of 94° C. for one minute, 36° C. for one minute and 72° C. for two minutes. Then, the sample mixture was applied into 1×3–5 mm gelslot in 1.5% agarose with 1× TAE buffer, and subjected to an hour of electrophoresis with a voltage gradient of 5 V/cm. After the electrophoresis, the gel was stained for an hour with 0.5 g/ml of ethidium bromide, and DNA bands were detected by irradiating ultraviolet rays of 300 to 320 nm (3) Identification of the nucleic acid marker DNA fragments amplified from the DNA extracts 2) to 4) listed in (1)-(a) above were compared to identify DNA fragments which were present in the DNAs of 2) and 4) with rice blast resistance gene Pi-bbut not present in the DNA of 3) without the gene Pi-b (FIG. 6). Furthermore, the DNA fragments located within 1.0 cM (corresponding to about 100–200 kb) from the gene Pi-b were identified F$_2$ analysis of Norin 22 (without Pi-b)×BL1 (with Pi-b).

A nucleic acid marker b-1 for the rice blast resistance gene Pi-b was thus obtained. This marker b-1 is a DNA sequence having a total length of from 800 to 1,400 b, and has the sequence No. 1 nucleotide sequence or its homologous sequence at the both ends of it.

It was confirmed that this marker b-1 was identifiable also by the comparison of PCR amplified fragments of the DNAs of 5) of each cultivar, as a simplified version of the above-mentioned method.

Figure 7:
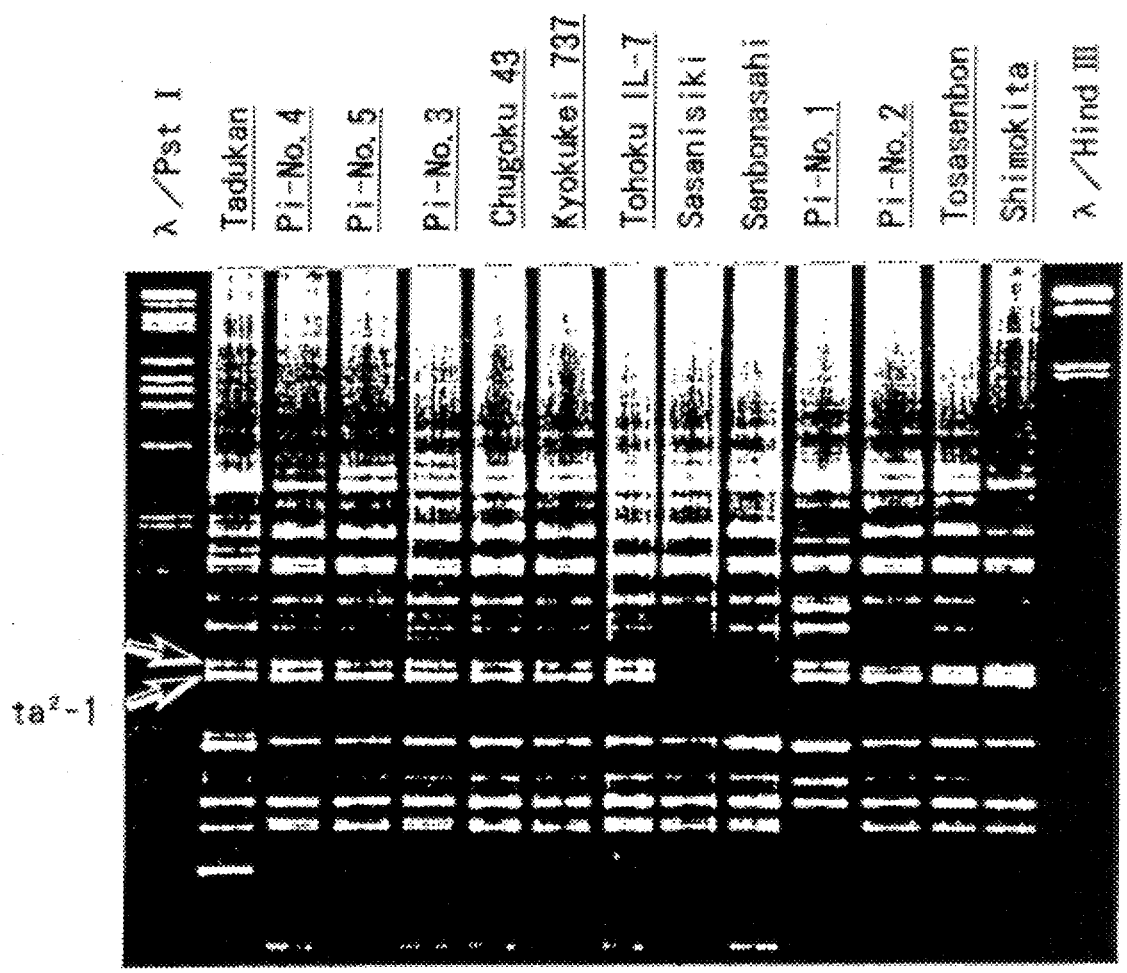
FIG. 7 is rapid marker ta2-1 bands (arrow) amplified from the FIG. 3 related cultivars. Bands ta2-1 are specific to the all of the cultivars with Pi-ta$^2$ and Pi-ta as indicated by underlining.

It was also confirmed that this marker b-1 was applicable as a satisfactory marker of Pi-b even for the rice genome library 1), of the rice cultivars with the gene Pi-b. Thus amplified bands ta2-1 are shown in FIG. 7.

EXAMPLE 2

Figure 3:
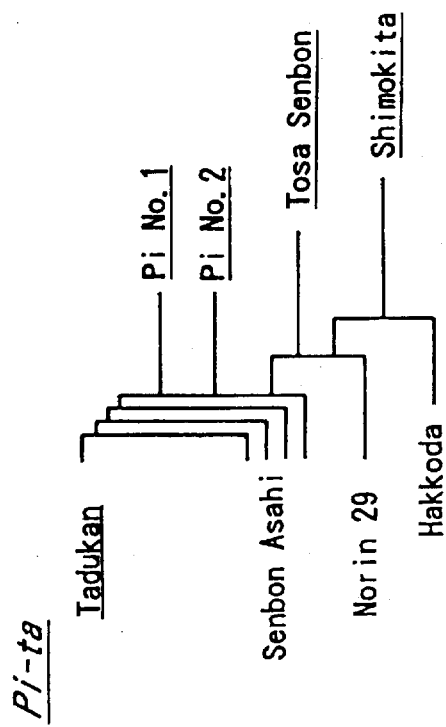
FIG. 3 is a pedigree illustrating the introduction of rice blast resistance genes Pi-ta$^2$ and Pi-ta into japonica cultivars. Underlining indicate cultivars with the resistance gene.
Figure 3:
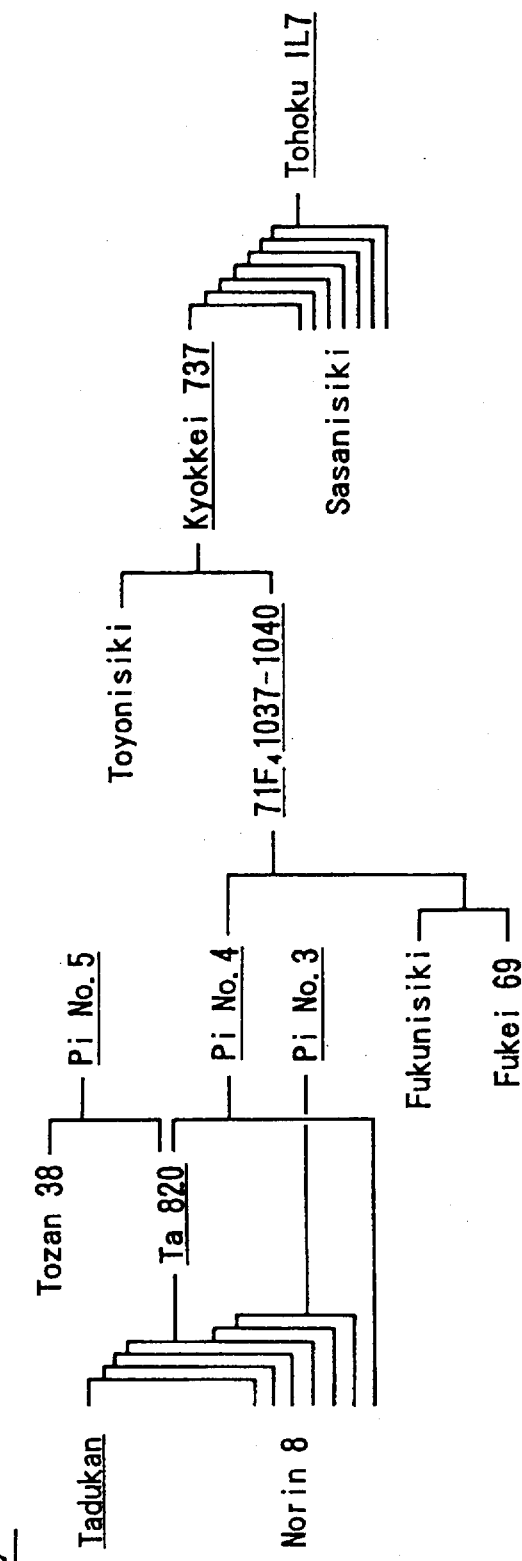

A nucleic acid marker for the rice blast resistance gene Pi-ta$^2$ was identified in the same manner as in Example 1, except that a synthetic oligonucleotide PCR primer comprising sequence No. 2 nucleotide sequence and rice cultivars with the Pi-ta or Pi-ta$^2$ related pedigree of FIG. 3 were used.

Thus obtained marker ta2-1 is a DNA sequence having a total length of from 400 to 600 bp, with the nucleotide sequence of No. 2 or homologous sequences at the both ends of it.

Now, the following paragraphs describe some Tests carried out to investigate characteristics of the markers b-1 and ta2-1 obtained in the above-mentioned Examples 1 and 2.

Test 1

For the marker b-1, its behavior was tested for the near isogenic lines (NILs) into which rice blast resistance genes were introduced by repeated backcrosses from indica rice cultivars. The Pi-b gene derived from an indica rice cultivars has been introduced into ten lines through repeated backcrosses as shown in FIG. 1. The extent of the chromosome introduced from the indica donor to these NILs were examined using the neighboring RFLP (restriction fragment polymorphism) markers (Saito et al.: Jpn. J. Breed., vol. 41, 665–670; Kurata et al., 1992: Rice Genet, Newslett., vol. 9, 130–132), and compared with the labeling marker (b-1) obtained in Example 1.

Figure 2:
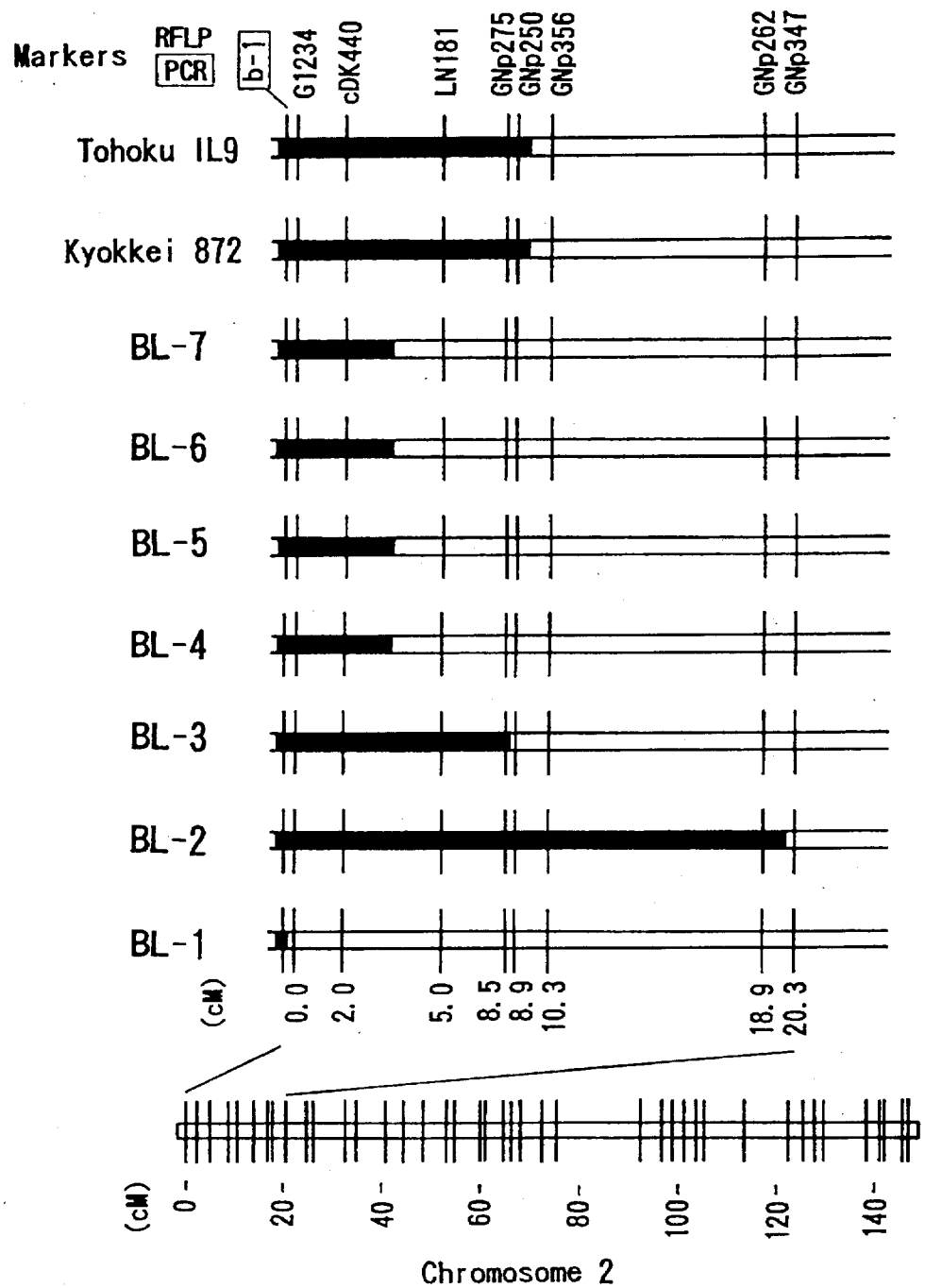
FIG. 2 is a schematic view illustrating the rice second chromosome of the near isogenic lines with Pi-b gene. Black parts indicates the region derived from indica donor.

DNAs were extracted from each of the cultivate shown in FIG. 1 to carry out Southern blots with RFLP markers of the upper end potion of the second chromosome, and it was investigated what portion of the chromosome of the indica donor parents were inherited into these NILs, by checking these markers to be japonica or indica type (FIG. 2). According to the results (FIG. 2), two RFLP markers showed the indica type for eight out of nine NIL cultivars, but there were no marker which showed the indica type for all tested NILs. A PCR analysis was conducted, on the other hand, using DNAs extracted from all the cultivars in FIG. 1, in the same manner as in Examples: b-1 band exhibited the indica type in all the cultivate containing Pi-b, including nine cultivars of NILs. In other words, the marker b-1 showed a better correlation with the presence of the rice blast resistance gene Pi-b than any PFLP markers known to date (Kurata et al., 1992: Rice Genet. Newslett., vol.9, 130–132).

Test 2

A test was carried out on the marker ta2-1, in the same manner as in Test 1.

Rice resistance genes Pi-ta$^2$ and Pi-ta, derived from an indica cultivar, are known to occupy the same locus (Kiyosawa, 1967: Jpn. J. Breed., vol.17, 165–172). For this donor parent, recurrent parent's and near isogenic lines in the pedigree (FIG. 3), their types of polymorphism were investigated in the RAPD labelling marker ta2-1 and the neighboring RFLP markers (Saito et al., 1991: Jpn. J. Breed., vol. 41, 665–670), and it was examined what portion of chromosome was introduced from the indica donor and approximate positions in the genetic map were determined for the resistance genes and ta2-1 (FIG. 4).

Figure 4:
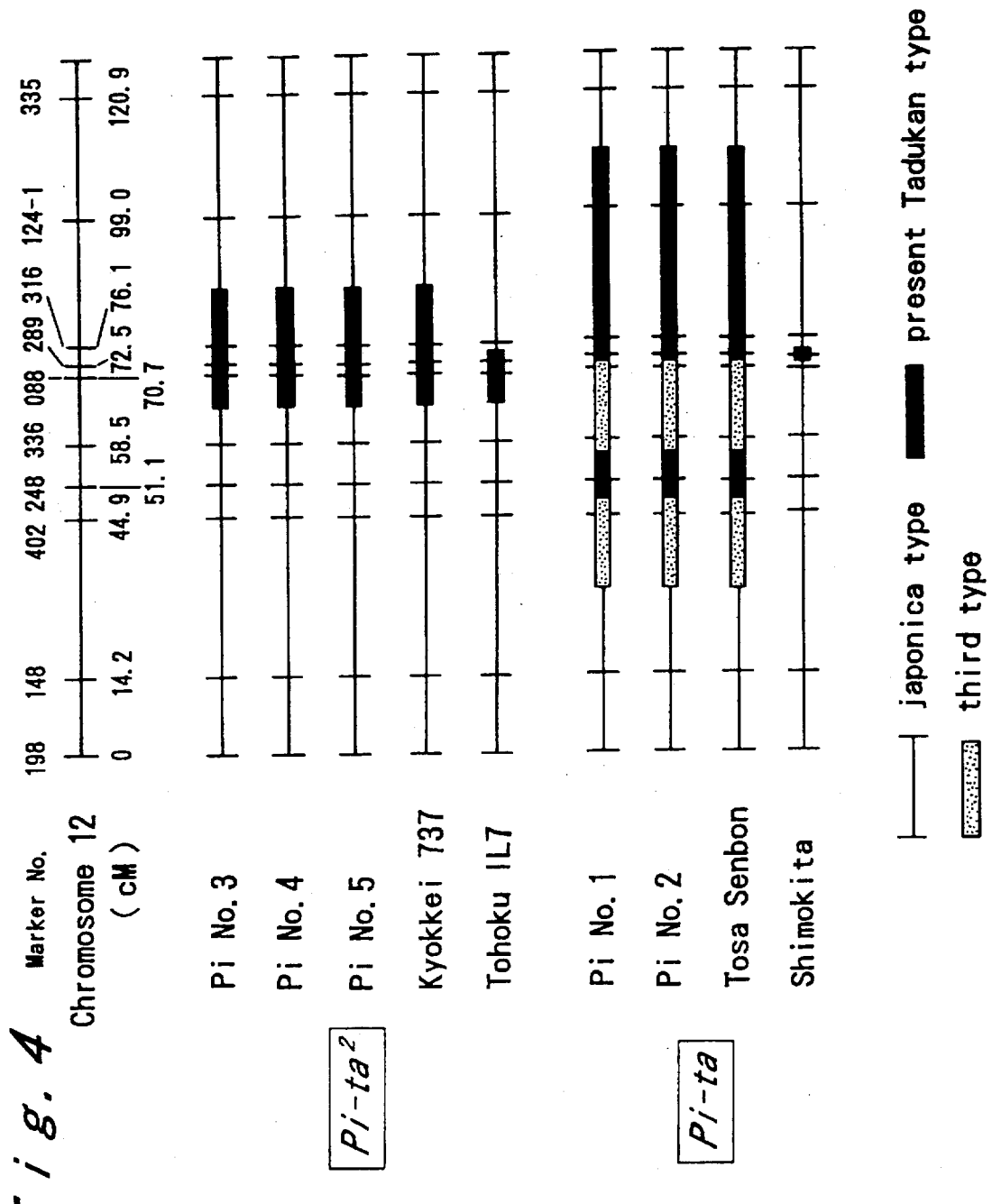
FIG. 4 is a schematic view of the rice twelfth chromosome of the near isogenic lines with Pi-ta$^2$ and Pi-ta genes. Black and gray parts indicate the region derived from indica donor.

DNAs were extracted from each of the cultivars shown in FIG. 3, to carry out Southern blots with the RFLP markers on the twelfth chromosome (Saito et al., 1991) to investigate what portion of the chromosome was inherited from the indica donor to each of the NILs (FIG. 4). A PCR analysis was conducted, on the other hand, using these extracted DNAs in the same manner as in Examples: the ta2-1 band showed the indica type for all the cultivars with Pi-ta$^2$. Therefore, the position of ta2-1 on the chromosome map was estimated to be within the shadowed range in FIG. 4.

While some of the conventional RFLP markers showed a similar behavior as ta2-1, it is more difficult for the conventional markers to test their polymorphism than ta2-1, and takes three times more time.

Test 3

An F$_2$ analysis was carried out to determine the genetic distance between the rice blast resistant gene Pi-b and the labelling marker b-1.

BL-1, a cultivar with the rice blast resistance gene Pi-b, and Norin 22, a cultivar without Pi-b were mated, and many second generation individuals (F$_2$) were obtained. Using this F$_2$ group, an experiment was carried out to determine a recombination ratio and the genetic distance between the rice blast resistance gene Pi-b and the labelling marker b-1.

About 400 of F$_2$ individuals were grown, and at about the five to six-leaf period, a suspension of rice blast strain Hoku-1 conidia of 1×10$^5$/ml was spray-inoculated to the leaves. The inoculated leaves were left at 25° C. relative humidity of 100% for 24 hours, then brought to a greenhouse. After 7 days from inoculation, resistance or susceptibility of the individuals was diagnosed from the occurence and severeness of lesions on the leaves.

DNA was extracted from each of 85 individuals determined to be susceptible, and for all of them the PCR was carried out in the same manner as in Examples, to check the pattern of b-1 being indica or japonica type. As the result, no recombination was found between b-1 and Pi-b, and the genetic distance between them was estimated to be under 0.5 cM. This distance corresponds to a physical distance of less than 50–100 kb, on the assumption of the rice genome size to be 200–420 Mb, and the total length to be about 2,000 cM on the chromosome map (Saito et al., 1991). This is a very short distance considering the easy availability of 200 to 300 kb genome fragments in yeast artificial chromosome (YAC), and positional cloning will be sufficiently possible for this distance.

Only susceptible individuals were used in the F$_2$ analysis to avoid occurence of susceptible individuals apparently showing no lesion and diagnosed to be resistant, due to insufficient spray-inoculation. In contrast, the possibility that a resistant individual show many necrotic lesions is very low. This consequently leads to a higher accuracy for the diagnosis of the phenotypes. As the resistance genes are dominant, susceptible individuals are recessive homologs of japonica type at the locus of gene Pi-b, and the band pattern of b-1 marker in the neighborhood are expected to be of the japonica type. Therefore, even one recombination of the two homologous chromosomes to the indica type can be easily detected. As it is possible to detect recombination in twice numbers of chromosomes of individuals, efficiency of measurement of the recombination ratio becomes also twice as high. These two advantages are very important for determining the distance between two genes of very low recombination ratio.

Test 4

An F$_2$ analysis was conducted to determine the genetic distance between the rice blast resistance gene Pi-ta$^2$ and the labelling marker ta2-1.

PiNo. 4, a cultivar with the rice blast resistance gene Pi-ta$^2$, and Norin 22, a cultivar without Pi-ta$^2$, were mated, and many second generations (F$_2$) seeds were obtained. Using the F$_2$ individuals, an experiment was carried out to determine the recombination ratio between the rice blast resistance gene Pi-ta$^2$ and the marker ta2-1, and the genetic distance between them.

About 400 of F$_2$ individuals were grown, and at about the five-leaf period, a suspension of rice blast strain Hoku-1 conidia of the concentration of 1×10$^5$/ml was spray-inoculated to leaves. The inoculated leaves were left at 25° C. relative humidity of 100% for 24 hours, and then brought into a greenhouse. After 7 days from inoculation, resistant and susceptible of the individuals were diagnosed from the occurence and severeness of lesions on the leaves1.

DNA was extracted from each of 85 individuals determined to be susceptible, and for all of them the PCR was carried out in the same manner as in Examples, to check the pattern of ta2-1 is indica or japonica type. As the result, no recombination was found between ta2-1 and Pi-ta$^2$, and the genetic distance between them was estimated to be 0.5 cM.

This distance corresponds to a physical distance of less than 50–100 kb on the chromosome map. This is a very short distance considering the easy availability of 200 to 300 kb genome fragment in yeast artificial chromosome (YAC), and positional cloning will be sufficiently possible for this distance.

Test 5

The position of the Rapd marker b-1 on the RFLP map was determined.

Figure 5:
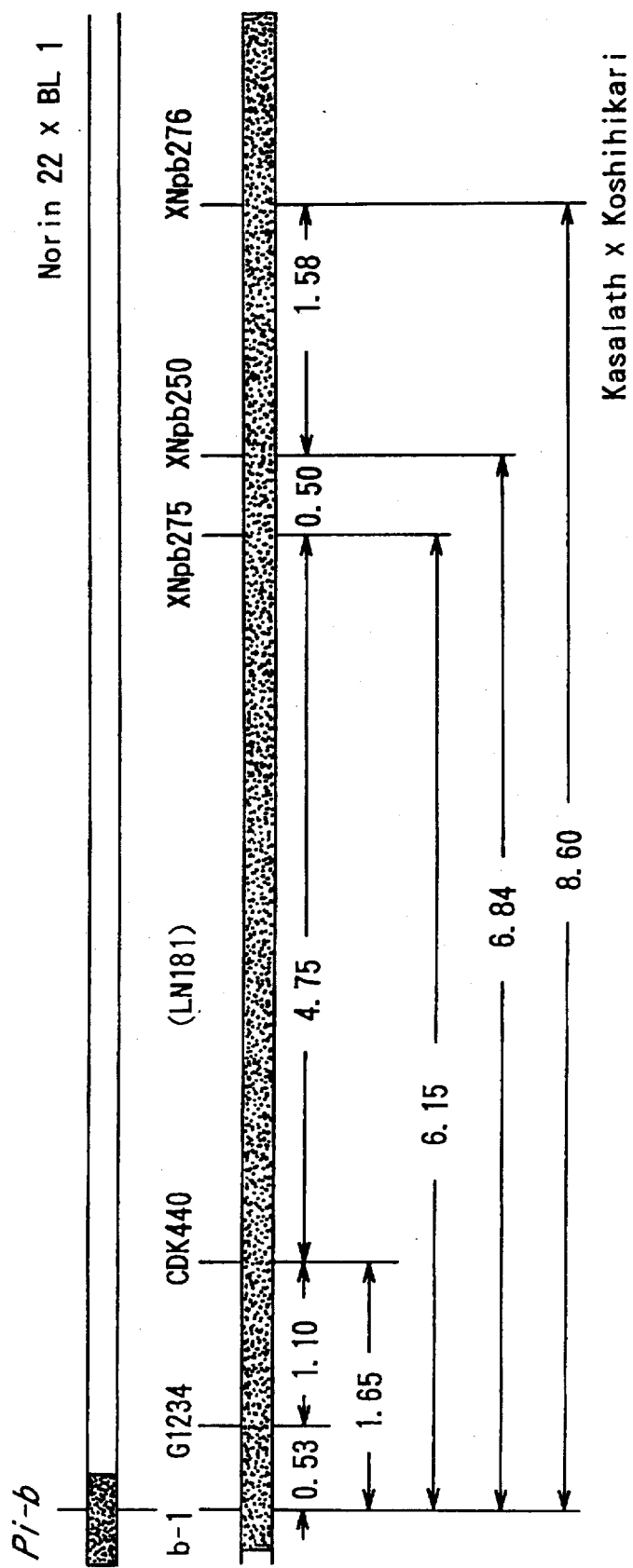
FIG. 5 is a mapping of rice resistance gene Pi-b on an RFLP map via the cosegregating RAPD marker b-1. The distances are presented in cM.

$F_2$ of the crossing between BL-1 and Norin 22 were used for analysis as described in Test 3. In the chromosome 2 of BL-1, only very limited extent has been derived from the indica donor, and the RFLP markers so far available are not present therein. It is therefore impossible to determine the position of Pi-b on the RFLP map through this $F_2$ analysis. However, the position of Pi-b on the RFLP map could be indirectly determined from the position of b-1 which was cosegregating with Pi-b, by using $F_2$ of the crossing of Kasalath (indica) and Koshihikari (japonica), both of them without Pi-b gene, by mapping b-1 on the RFLP map (FIG. 5).

More specifically, nucleic acids were extracted from each of 85 individual of $F_2$ resulting from the crossing of Kasalath and Koshihikari. The recombination ratios between the RFLP markers Saito et al. (1991) and Kurata et al. (1992) and the RAPD marker b-1 were measured, and the position of b-1 on the RFLP map was determined as shown in FIG. 5. Pi-b is considered to be at the same position. The polymorphic type of b-1 was determined by Southern hybridization using the isolated b-1 band nucleic acid as probes.

It was confirmed, from the results of the above-mentioned Tests 1 to 5, that the nucleic acid markers b-1 and ta2-1 obtained in the Examples 1 and 2 were located at a distance of under 0.5 cM and of 0.5 cM, respectively, from the rice blast resistance genes Pi-b and Pi-ta$^2$, and are good labelling markers for the genes Pi-b and Pi-ta$^2$.

[Sequence List]

Sequence No.: 1
Length: 10
Type: nucleic acid
Strandedness: single strand
Topology: linear
Molecule Type: synthetic DNA
Sequence
  GTGAT CGCAG 10

Sequence No.: 2
Length: 10
Type: nucleic acid
Strandedness: single strand
Topology: linear
Molecule Type: synthetic DNA
Sequence
  TCGCC AGCCA 10

---

---

What is claimed is:

1. A nucleic acid marker for rice blast resistance gene Pi-b, which is:
   (a) isolated from rice genomic DNA;
   (b) a DNA sequence having a total length of from 400 to 660 bases, and having at both 3' and 5' ends the base sequence shown in SEQ ID No. 1; and
   (c) located within a distance of 1.0 centiMorgan from the gene Pi-b.

2. A nucleic acid marker from rice blast resistance gene Pi-ta$^2$ or Pi-ta$^2$, which is:
   (a) isolated from rice genomic DNA;

(b) a DNA sequence having a total length of from 400 to 660 bases, and having at both 3' and 5' ends the base sequence shown in SEQ ID No. 2; and (c) located within a distance of 1.0 centiMorgan from the gene Pi-ta or Pi-ta².

3. A nucleic acid marker for rice blast resistance gene Pi-b, which is isolated from a region between the gene Pi-b and the nucleic acid marker of claim 1.

4. A nucleic acid marker for rice blast resistance gene Pi-ta or Pi-ta², which is isolated from a region between the gene Pi-ta or Pi-ta² and the nucleic acid marker of claim 2.

5. A rice blast resistance gene Pi-b, which is isolated from a region within a distance of 1.0 centiMorgan from the nucleic acid marker of claim 1 or 3.

6. A rice blast resistance gene Pi-ta or Pi-ta², which is isolated from a region within a distance of 1.0 centiMorgan from the nucleic acid marker of claim 2 or 4.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 10 bases
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:1:

GTGAT CGCAG    10

( 2 ) INFORMATION FOR SEQ ID NO:2:

( i ) SEQUENCE CHARACTERISTICS:
        ( A ) LENGTH: 10 bases
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:2:

TCGCC AGCCA    10